(12) United States Patent
Bowers (10) Patent No.: US 8,747,672 B2
(45) Date of Patent: Jun. 10, 2014

(54) PROCESS AND SYSTEM FOR RECOVERING PHOSPHORUS FROM WASTEWATER

(71) Applicant: Multiform Harvest Inc., Seattle, WA (US)

(72) Inventor: Keith E. Bowers, Seattle, WA (US)

(73) Assignee: Multiform Harvest Inc., Seattle, WA (US)

( * ) Notice: Subject to any disclaimer, the term of this patent is extended or adjusted under 35 U.S.C. 154(b) by 0 days.

(21) Appl. No.: 13/675,804

(22) Filed: Nov. 13, 2012

(65) Prior Publication Data

US 2013/0196403 A1   Aug. 1, 2013

Related U.S. Application Data (63) Continuation of application No. PCT/US2011/036514, filed on May 13, 2011.

(60) Provisional application No. 61/334,328, filed on May 13, 2010, provisional application No. 61/378,300, filed on Aug. 30, 2010.

(51) Int. Cl.
    *C02F 3/00*  (2006.01)
(52) U.S. Cl.
    USPC ........... 210/607; 210/768; 210/175; 210/903; 210/906; 210/749; 210/743; 210/181
(58) Field of Classification Search
    USPC ......... 210/607, 768, 175, 903, 906, 749, 743, 210/181
    See application file for complete search history.

(56) References Cited

U.S. PATENT DOCUMENTS

| | | | |
|---|---|---|---|
| 4,402,986 A | 9/1983 | Sinkoff | |
| 5,126,049 A | 6/1992 | Hallberg | |
| 7,604,740 B2 * | 10/2009 | Baur | 210/601 |
| 2003/0217968 A1 | 11/2003 | Goel | |
| 2005/0016919 A1 | 1/2005 | Hagino | |
| 2005/0051495 A1 | 3/2005 | Bowers | |
| 2007/0000836 A1 | 1/2007 | Elefritz, Jr. | |
| 2007/0044526 A1 | 3/2007 | Cabello-Fuentes | |
| 2008/0308505 A1 * | 12/2008 | Jansen et al. | 210/752 |
| 2009/0013742 A1 | 1/2009 | Zhang | |
| 2009/0078646 A1 | 3/2009 | Curtis | |
| 2009/0194476 A1 | 8/2009 | Baur | |
| 2010/0047134 A1 * | 2/2010 | Koch et al. | 422/111 |
| 2010/0170845 A1 | 7/2010 | Baur | |

(Continued)

FOREIGN PATENT DOCUMENTS

| | | |
|---|---|---|
| EP | 1 698 595 A1 | 9/2006 |
| JP | 11-010194 A | 1/1999 |

(Continued)

OTHER PUBLICATIONS

International Search Report and Written Opinion mailed Feb. 9, 2012, issued in corresponding International Application No. PCT/US2011/036514, filed May 13, 2011, 11 pages.

International Search Report and Written Opinion mailed May 1, 2012, issued in related International Application No. PCT/US2011/049769, filed Aug. 30, 2011, 9 pages.

(Continued)

*Primary Examiner* — Chester Barry (74) *Attorney, Agent, or Firm* — Christensen O'Connor Johnson Kindness PLLC (57) ABSTRACT

Methods and systems for recovery of phosphorus from wastewater and producing inorganic phosphorus complexes.

40 Claims, 8 Drawing Sheets

(56) References Cited

U.S. PATENT DOCUMENTS

| | | |
|---|---|---|
| 2012/0031849 A1 | 2/2012 | Britton |
| 2012/0261334 A1 | 10/2012 | Baur |
| 2012/0261338 A1 | 10/2012 | Kuzma |
| 2013/0062289 A1 | 3/2013 | Cote |

FOREIGN PATENT DOCUMENTS

| | | |
|---|---|---|
| KR | 10-0837698 B1 | 6/2008 |
| WO | 2005/049511 A1 | 6/2005 |
| WO | 2005/077834 A1 | 8/2005 |
| WO | 2008/108599 A1 | 9/2008 |
| WO | 2009/031796 A2 | 3/2009 |

OTHER PUBLICATIONS

International Preliminary Report on Patentability mailed Jan. 11, 2013, issued in related International Application No. PCT/US2011/049769, filed Aug. 30, 2011, 4 pages.

International Search Report and Written Opinion mailed Apr. 20, 2012, issued in related International Application No. PCT/US2011/049784, filed Aug. 30, 2011, 9 pages.

International Preliminary Report on Patentability mailed Mar. 14, 2013, issued in related International Application No. PCT/US2011/049784, filed Aug. 30, 2011, 8 pages.

International Search Report and Written Opinion mailed Oct. 4, 2012, issued in related International Application No. PCT/US2012/023882, filed Feb. 3, 2012, 7 pages.

* cited by examiner

PROCESS AND SYSTEM FOR RECOVERING PHOSPHORUS FROM WASTEWATER

CROSS-REFERENCES TO RELATED APPLICATIONS

This application is a continuation of International Application No. PCT/US2011/036514, filed May 13, 2011, which claims the benefit of U.S. Patent Application No. 61/334,328, filed May 13, 2010, and U.S. Patent Application No. 61/378,300, filed Aug. 30, 2010, each expressly incorporated herein by reference in its entirety.

FIELD OF THE INVENTION

The present invention relates in general to wastewater treatment and processes and systems for recovery of phosphorus from wastewater and for producing inorganic phosphorus complexes.

BACKGROUND OF THE INVENTION

The presence of dissolved phosphate in industrial effluents and wastewater is a long-standing problem in the art. Phosphorus (referred to herein as "P") is a non-renewable resource and an important non-substitutable macronutrient, existing in nature as phosphates in various inorganic or organic forms, and ranging from the simple to the very complex in terms of molecular structure. Because P is essential for all biological processes, there is concern that the current demand and exploitation (total annual production is about 20 million tons of P, derived from roughly 140 million tons of rock concentrates) of this non-renewable resource is not sustainable. Nearly all the P used globally is mined from a relatively small number of commercially-exploitable deposits, and it has been estimated that the global economic P reserves may last about 100 years at the current rate of extraction. Therefore, the world's P resources are finite and should be used efficiently and in a sustainable way. Additionally, aside from the non-renewable resource aspect, there is need to improve P management, particularly from the environment protection perspective because, for example, P-enrichment in receiving waters is associated with harmful algae blooms that affect the health and vitality of wetlands and marine environments. Therefore, there is a pronounced need in the art to develop methods for increasing the life expectancy of the world's limited P resources. There is a pronounced need in the art to develop methods for recovery and recycling of P from industrial effluents and wastewater.

Art-recognized P removal technologies applied to wastewater include chemical and biological processes. One chemical technology for P removal and recovery is crystallization of P in the form of struvite (magnesium ammonium phosphate hexahydrate or $MgNH_4PO_4 \cdot 6H_2O$). Struvite is crystalline and thus well suited for formation from effluent streams. In addition, as a granular product struvite is more compact than other chemical precipitates, and it performs well as a slow-release fertilizer. Struvite formation requires reaction between three soluble ions in solution, $Mg^{2+}$, $NH_4^+$ and $PO_4^{3-}$, to form precipitates with low solubility (struvite has a $pK_{sp}$ of 12.6). Struvite precipitation is controlled by pH, supersaturation, and presence of impurities, such as calcium. High pH (e.g., pH 8.5) and supersaturation of the three ions are favorable to struvite formation.

As part of secondary sewage treatment, primary treated sewage is treated with air or oxygen. In the activated sludge process, microorganisms utilize oxygen to metabolize the incoming waste sewage thereby forming a mixture of microorganisms and sewage (mixed liquor). This mixture is conducted to settling tanks for concentration to provide concentrated activated sludge. A majority of the sludge is returned to the activated sludge process and a separate portion of this sludge (waste activated sludge) is removed from the activated sludge process and conducted to a sludge handling system for further treatment and disposal.

In a typical wastewater treatment process, waste activated sludge is conducted to a first centrifuge (or other thickening apparatus) for thickening, where the liquids are tapped off and returned to the wastewater plant for treatment and the resultant thickened sludge is conducted to an anaerobic digester with other sludge where it remains for a period of time before being conducted to a second centrifuge (or other dewatering apparatus) for dewatering. Struvite tends to form in the digester and other downstream equipment because of the ammonia, magnesium and phosphorus present in the process streams. This struvite is impractical to harvest and also has the deleterious effect of being deposited on surfaces in the process system components. The second centrifuge (or other dewatering apparatus) produces additional dewatered sludge and liquids that are rich in ammonia and phosphorus.

U.S. Pat. No. 7,604,740 describes a wastewater treatment method. In the method, a first mixture of waste solids and microorganisms containing phosphorus and magnesium are treated by first inducing the mixture microorganisms to release phosphorus and magnesium that is then tapped off as the mixture is thickened, to produce phosphorus and magnesium-rich liquid and phosphorus and magnesium-reduced treated mixture. The treated mixture is placed in an anaerobic digester where ammonia is formed, but sparingly combines with phosphorus or magnesium because the concentration of these materials has been greatly reduced. Next, the high-ammonia mixture is dewatered to produce an ammonia-rich liquid. Struvite is then formed by combining the ammonia-rich liquid with the phosphorus and magnesium-rich liquid. However, controlling the formation of struvite through the combination of two variable process streams is problematic.

Despite the advances in removing phosphorus from wastewater through the formation and recovery of struvite, a need exists for improved methods and devices for wastewater treatment and struvite recovery that does not involve combining two variable process streams. The present invention seeks to fulfill this need and provides further related advantages.

SUMMARY OF THE INVENTION

The present invention provides methods and systems for treating wastewater and producing inorganic phosphorus. In the methods and systems, inorganic phosphorus is formed from phosphorus in the wastewater by the combination of a phosphorus- and magnesium-rich liquid stream with ammonia. The phosphorus- and magnesium-rich liquid stream is a direct product from the release of phosphorus and magnesium from phosphorus- and magnesium-containing microorganisms in the wastewater. The ammonia that is combined with the phosphorus- and magnesium-rich liquid stream is not an untreated ammonia-rich liquid process stream, for example, an ammonia-rich, phosphorus- and magnesium-reduced liquid obtained by solids separation of the output from anaerobic digestion of a phosphorus- and magnesium-reduced mixture. Rather the ammonia that is combined with the phosphorus- and magnesium-rich liquid stream is either ammonia from an external source or derived from an ammonia-rich process stream conducted from an inorganic phosphorus reactor, optionally further treated by, for example, stripping or separating ammonia from the stream.

In one aspect, the invention provides a method for producing inorganic phosphorus from wastewater. In one embodiment, the method comprises:

(a) thickening a phosphorus- and magnesium-containing mixture derived from microorganisms induced to release phosphorus and magnesium to provide a phosphorus- and magnesium-rich liquid and a phosphorus- and magnesium-reduced mixture;

(b) conducting the phosphorus- and magnesium-rich liquid to a first inorganic phosphorus reactor;

(c) anaerobically treating the phosphorus- and magnesium-reduced mixture to provide an ammonia-rich, phosphorus- and magnesium-reduced mixture;

(d) separating a first ammonia-rich, phosphorus- and magnesium-reduced liquid from the ammonia-rich, phosphorus- and magnesium-reduced mixture;

(e) conducting the first ammonia-rich, phosphorus- and magnesium-reduced liquid to a second inorganic phosphorus reactor to provide inorganic phosphorus and a second ammonia-rich, phosphorus- and magnesium-reduced liquid; and (f) adding ammonia to the phosphorus- and magnesium-rich liquid in the first inorganic phosphorus reactor to provide inorganic phosphorus.

In one embodiment, the ammonia added to the phosphorus- and magnesium-rich liquid in the first inorganic phosphorus reactor is derived from the second ammonia-rich, phosphorus- and magnesium-reduced liquid.

In one embodiment, the ammonia added to the phosphorus- and magnesium-rich liquid in the first inorganic phosphorus reactor is derived from the inorganic phosphorus provided in the second inorganic phosphorus reactor.

In one embodiment, the ammonia added to the phosphorus- and magnesium-rich liquid in the first inorganic phosphorus reactor is from an external source.

In one embodiment, the ammonia added to the phosphorus- and magnesium-rich liquid in the first inorganic phosphorus reactor is an ammonia-rich, phosphorus- and magnesium-reduced liquid from the second inorganic phosphorus reactor.

In another embodiment, the invention provides a method for treating wastewater and producing inorganic phosphorus, comprising:

(a) inducing a mixture of microorganisms containing phosphorus and magnesium to release phosphorus and magnesium to provide a treated mixture that includes phosphorus and magnesium;

(b) thickening the treated mixture to provide a phosphorus- and magnesium-rich liquid and a phosphorus- and magnesium-reduced mixture;

(c) conducting the phosphorus- and magnesium-rich liquid to a first inorganic phosphorus reactor;

(d) anaerobically treating the phosphorus- and magnesium-reduced mixture to provide an ammonia-rich, phosphorus- and magnesium-reduced mixture;

(e) separating a first ammonia-rich, phosphorus- and magnesium-reduced liquid from the ammonia-rich, phosphorus- and magnesium-reduced mixture;

(f) conducting the first ammonia-rich, phosphorus- and magnesium-reduced liquid to a second inorganic phosphorus reactor and adjusting the pH to provide inorganic phosphorus and a second ammonia-rich, phosphorus- and magnesium-reduced liquid;

(f) conducting the second ammonia-rich, phosphorus- and magnesium-reduced liquid to an ammonia stripper to provide ammonia and an ammonia-reduced, phosphorus-, and magnesium-reduced liquid; and (g) adding the ammonia to the phosphorus- and magnesium-rich liquid in the first inorganic phosphorus reactor to provide inorganic phosphorus.

In a further embodiment, the invention provides a method for treating wastewater and producing inorganic phosphorus, comprising:

(a) inducing a mixture of microorganisms containing phosphorus and magnesium to release phosphorus and magnesium to provide a treated mixture that includes phosphorus and magnesium;

(b) thickening the treated mixture to provide a phosphorus- and magnesium-rich liquid and a phosphorus- and magnesium-reduced mixture;

(c) conducting the phosphorus- and magnesium-rich liquid to a first inorganic phosphorus reactor;

(d) anaerobically treating the phosphorus- and magnesium-reduced mixture to provide an ammonia-rich, phosphorus- and magnesium-reduced mixture;

(e) separating a first ammonia-rich, phosphorus- and magnesium-reduced liquid from the ammonia-rich, phosphorus- and magnesium-reduced mixture;

(f) conducting the first ammonia-rich, phosphorus- and magnesium-reduced liquid to a second inorganic phosphorus reactor to provide inorganic phosphorus; and (g) conducting a portion of the inorganic phosphorus from the second inorganic phosphorus reactor to a heater to provide magnesium, phosphorus, and ammonia and water, wherein the ammonia and water are added to the phosphorus- and magnesium-rich liquid in the first inorganic phosphorus reactor to provide inorganic phosphorus.

In one embodiment, the ammonia and water from the heater are conducted to a separator to provide gaseous ammonia, which is then optionally combined with water, and added to the phosphorus- and magnesium-rich liquid in the first inorganic phosphorus reactor.

In another embodiment, the invention provides a method for treating wastewater and producing inorganic phosphorus, comprising:

(a) inducing a mixture of microorganisms containing phosphorus and magnesium to release phosphorus and magnesium to provide a treated mixture that includes phosphorus and magnesium;

(b) thickening the treated mixture to provide a phosphorus- and magnesium-rich liquid and a phosphorus- and magnesium-reduced mixture;

(c) conducting the phosphorus- and magnesium-rich liquid to a first inorganic phosphorus reactor;

(d) adding ammonia to the phosphorus- and magnesium-rich liquid in the first inorganic phosphorus reactor to provide inorganic phosphorus;

(e) anaerobically treating the phosphorus- and magnesium-reduced mixture from step (b) to provide a ammonia-rich, phosphorus- and magnesium-reduced mixture;

(f) separating a first ammonia-rich, phosphorus- and magnesium-reduced liquid from the ammonia-rich, phosphorus- and magnesium-reduced mixture; and (g) conducting the first ammonia-rich, phosphorus- and magnesium-reduced liquid to a second inorganic phosphorus reactor to provide inorganic phosphorus.

In a further embodiment, the invention provides a method for treating wastewater and producing inorganic phosphorus, comprising:

(a) inducing a mixture of microorganisms containing phosphorus and magnesium to release phosphorus and magnesium to provide a treated mixture that includes phosphorus and magnesium;

(b) separating the treated mixture into a phosphorus- and magnesium-rich liquid and a phosphorus- and magnesium-reduced mixture;

(c) conducting the phosphorus- and magnesium-rich liquid to a first inorganic phosphorus reactor;

(d) anaerobically treating the phosphorus- and magnesium-reduced mixture to provide an ammonia-rich, phosphorus- and magnesium-reduced mixture;

(e) separating the ammonia-rich, phosphorus- and magnesium-reduced mixture to provide biosolids and a first ammonia-rich, phosphorus- and magnesium-reduced liquid;

(f) conducting the first ammonia-rich, phosphorus- and magnesium-reduced liquid to a second inorganic phosphorus reactor to provide inorganic phosphorus and to provide a second ammonia-rich, phosphorus- and magnesium-reduced liquid; and (g) conducting the second ammonia-rich, phosphorus- and magnesium-reduced liquid to the first inorganic phosphorus reactor to provide inorganic phosphorus and a phosphorus- and magnesium-reduced liquid.

In one embodiment, the phosphorus- and magnesium-reduced liquid is conducted to the process headworks.

In one embodiment, magnesium, ammonia, and pH boosters are independently, optionally added to the first and/or second inorganic phosphorus reactors.

The above methods can further include the step of collecting inorganic phosphorus from the inorganic phosphorus reactors.

In the above methods, the inorganic phosphorus is a magnesium/phosphate complex. In one embodiment, the inorganic phosphorus is a magnesium ammonium phosphate hexahydrate, such as struvite.

In another aspect, the invention provides systems for treating wastewater and producing inorganic phosphorus.

In one embodiment, the system for producing inorganic phosphorus from wastewater, comprises:

(a) a first solids separator for thickening a phosphorus- and magnesium-containing mixture;

(b) a first inorganic reactor, the reactor having a conduit for receiving ammonia;

(c) a first conduit intermediate the first solids separator and the first inorganic phosphorus reactor;

(d) a digester;

(e) a second conduit intermediate the first solids separator and the digester;

(f) a second solids separator;

(g) a third conduit intermediate the digester and the second solids separator.

(h) a second inorganic reactor; and (i) a fourth conduit intermediate the second solids separator and the second inorganic phosphorus reactor.

In one embodiment, the first solids separator further comprises a conduit for receiving a phosphorus- and magnesium-containing mixture.

In one embodiment, the second solids separator further comprises a conduit for conducting biosolids from the solids separator.

In one embodiment, the system further comprises:

(a) an ammonia stripper intermediate the first and second inorganic phosphorus reactors;

(b) a conduit intermediate the second inorganic phosphorus reactor and the stripper; and (c) a conduit intermediate the stripper and the first inorganic phosphorus reactor and the stripper.

In one embodiment, the system further comprises:

(a) a heater intermediate the first and second inorganic phosphorus reactors;

(b) a conduit intermediate the second inorganic phosphorus reactor and the heater;

(c) an ammonia separator intermediate the heater and the first inorganic phosphorus reactor;

(d) a conduit intermediate the heater and the separator; and (e) a conduit intermediate the separator and first inorganic phosphorus reactor.

In one embodiment, the second inorganic phosphorus reactor further comprises a conduit for conducting a second ammonia-rich, phosphorus- and magnesium-reduced liquid from the second inorganic phosphorus reactor, and the first inorganic phosphorus reactor further comprises a conduit for receiving ammonia.

In one embodiment, the system further comprises a conduit intermediate the second inorganic phosphorus reactor and the first inorganic phosphorus reactor; and the first inorganic phosphorus reactor further comprises a conduit for conducting a phosphorus- and magnesium-reduced liquid from the reactor.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

The invention provides processes for removing and recovering of phosphorus from wastewater through the formation of inorganic phosphorus (e.g., struvite). The processes advantageously remove phosphorus from wastewater treatment streams and provide inorganic phosphorus as a valuable byproduct.

The present invention provides a method for handling nutrients in wastewater with the goals of reducing phosphorus and magnesium in the mixture fed to a wastewater digester and reducing struvite scale formation in the digester where ammonia, a starting material for making struvite, is released. Other objectives achieved by the process include removing phosphorus from the system in mineral (inorganic) form rather than biosolids to reduce volume and obtain more valuable phosphorus-containing products; minimizing the linking of different process streams for improved process flexibility and ready recovery from upsets; and reducing ammonia content in the final liquid.

As noted above, the present invention provides a method for treating wastewater and producing inorganic phosphorus. In the method, inorganic phosphorus is formed from phosphorus in the wastewater by the combination of a phosphorus- and magnesium-rich liquid stream with ammonia. The phosphorus- and magnesium-rich liquid stream is a direct product from the release of phosphorus and magnesium from phosphorus- and magnesium-containing microorganisms in the wastewater. The ammonia that is combined with the phosphorus- and magnesium-rich liquid stream is not an ammonia-rich liquid stream, as in the process described in U.S. Pat. No. 7,604,740. Rather the ammonia that is combined with the phosphorus- and magnesium-rich liquid stream is either ammonia from an external source or derived from an ammonia-rich process stream from an inorganic phosphorus reactor, optionally further treated by, for example, stripping or separating ammonia from an ammonia-rich process. By the use of ammonia, rather than an ammonia-rich process stream, as a feedstock in the formation of inorganic phosphorus, the method of the invention provided improved control over the inorganic phosphorus formation reaction.

In the methods and systems of the invention, ammonia is combined with phosphorus and magnesium to produce inorganic phosphorus (e.g., struvite). It will be appreciated that the nature of the ammonia will depend on the pH of the environment of the process streams in which the ammonia is present. For example, at lower pH, ammonia will be in the form of ammonium ($NH_4^+$) and can be associated with counterions (e.g., sulfate, $SO_4^{2-}$).

Figure 1:
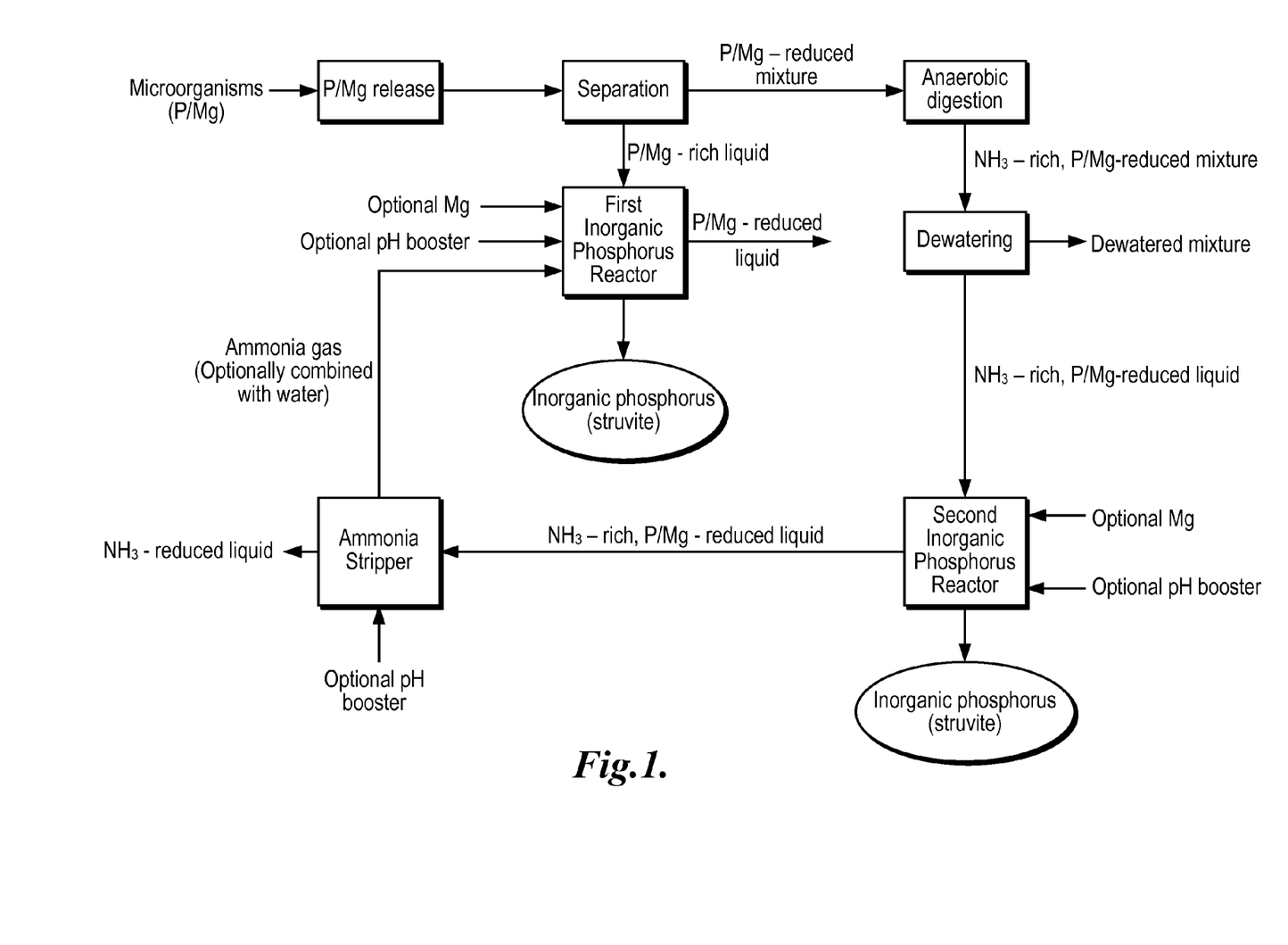
FIG. 1 is a schematic illustration of a representative method of the invention for treating wastewater and producing inorganic phosphorus.

A schematic illustration of a first embodiment of the method of the invention for treating wastewater and producing inorganic phosphorus is shown in FIG. 1. Referring to FIG. 1, a mixture of microorganisms containing phosphorus and magnesium are induced to release phosphorus and magnesium into liquid to provide a treated mixture that includes phosphorus and magnesium. The treated mixture is then thickened (dewatered) to provide a phosphorus- and magnesium-rich liquid and a phosphorus- and magnesium-reduced mixture. The phosphorus- and magnesium-rich liquid is conducted to a first inorganic phosphorus reactor. The phosphorus- and magnesium-reduced mixture is subjected to anaerobic digestion, where ammonia is released, to provide a first ammonia-rich, phosphorus- and magnesium-reduced mixture containing suspended solids in liquid. At this point substantially no combination of phosphorus and magnesium occurs because of the relatively low concentration of each and because the pH is low. The first ammonia-rich, phosphorus- and magnesium-reduced liquid is separated from the ammonia-rich, phosphorus- and magnesium-reduced mixture leaving behind a high biosolids portion. Separation of the liquid from the biosolids can be achieved by a variety of conventional means including gravity belts, filters, and centrifuges. The biosolids are removed from the system and the first ammonia-rich, phosphorus- and magnesium-reduced liquid is conducted to a second inorganic phosphorus reactor for inorganic phosphorus formation. There, magnesium is added, if needed, and pH is adjusted (e.g., addition of sodium hydroxide or other suitable pH booster), if necessary to provide inorganic phosphorus (e.g., struvite) and a second ammonia-rich, phosphorus- and magnesium-reduced liquid. The inorganic phosphorus is collected from the reactor and the high pH, second ammonia-rich, phosphorus- and magnesium-reduced liquid is conducted to an ammonium stripper, where the pH is adjusted as necessary (e.g., addition of sodium hydroxide or other suitable pH booster). The stripper provides a low ammonia, high pH liquid, which is removed from the system, and ammonia gas that is introduced into the first inorganic phosphorus reactor where it is combined with the phosphorus- and magnesium-rich liquid produced from the thickening of the treated mixture containing phosphorus and magnesium from the microorganism release step. As an alternative to introducing ammonia gas to the first inorganic phosphorus reactor, ammonia gas from the stripper can be combined with water and the resulting water containing ammonia can be added to the first reactor. In one embodiment, the ammonia stripper operating in combination with sulfuric acid provides ammonium sulfate combined in water as the ammonia source. Inorganic phosphorus (e.g., struvite) is formed in and ultimately collected from the first reactor. Additional ammonia or other suitable pH boosters can be added to the first reactor, as necessary. In one embodiment, a phosphorus- and magnesium-reduced liquid produced by the first reactor is conducted from the reactor.

The above method decouples the phosphorus- and magnesium-rich liquid from the ammonia-rich liquid (compare with U.S. Pat. No. 7,604,740 where the two process streams are combined) in the inorganic phosphorus forming step, which provides for greater process operational flexibility and increased process control. Because either stream can be subject to variations and upsets, their decoupling allows for each inorganic phosphorus reactor to be unaffected by perturbations in the other's process streams.

Thus, in one embodiment, the method includes the following steps:

(a) inducing a mixture of microorganisms containing phosphorus and magnesium to release phosphorus and magnesium to provide a treated mixture that includes phosphorus and magnesium;

(b) thickening the treated mixture to provide a phosphorus- and magnesium-rich liquid and a phosphorus- and magnesium-reduced mixture;

(c) conducting the phosphorus- and magnesium-rich liquid to a first inorganic phosphorus reactor;

(d) anaerobically treating the phosphorus- and magnesium-reduced mixture to provide an ammonia-rich, phosphorus- and magnesium-reduced mixture;

(e) separating a first ammonia-rich, phosphorus- and magnesium-reduced liquid from the ammonia-rich, phosphorus- and magnesium-reduced mixture;

(f) conducting the first ammonia-rich, phosphorus- and magnesium-reduced liquid to a second inorganic phosphorus reactor (optionally adjusting pH and optionally adding magnesium) to provide inorganic phosphorus (e.g., struvite) and a second ammonia-rich, phosphorus- and magnesium-reduced liquid;

(g) conducting the second ammonia-rich, phosphorus- and magnesium-reduced liquid to an ammonia stripper to provide ammonia and an ammonia-reduced, phosphorus-, and magnesium-reduced liquid; and (h) adding the ammonia produced in step (f) to the phosphorus- and magnesium-rich liquid in the first inorganic phosphorus reactor to provide inorganic phosphorus (e.g., struvite).

The above process offers advantages over conventional methods for recovering phosphorus from wastewater. For example, the addition of caustic in the second crystallizer (second inorganic phosphorus reactor) reduces the amount needed to be added in the stripper. The process also allows for the option of capturing at least a portion of the ammonia as ammonium sulfate, which is a useful fertilizer, because it is possible the ammonia demand by the first crystallizer will be less than that produced by the stripper. The ammonia addition to the first crystallizer can replace most or all of the caustic needed there, because in addition to providing the ammonia needed stoichiometrically for the reaction, it also is a powerful pH booster in this pH range. Ammonia (e.g., gas) from external sources can also be used to feed the first crystallizer.

Figure 2:
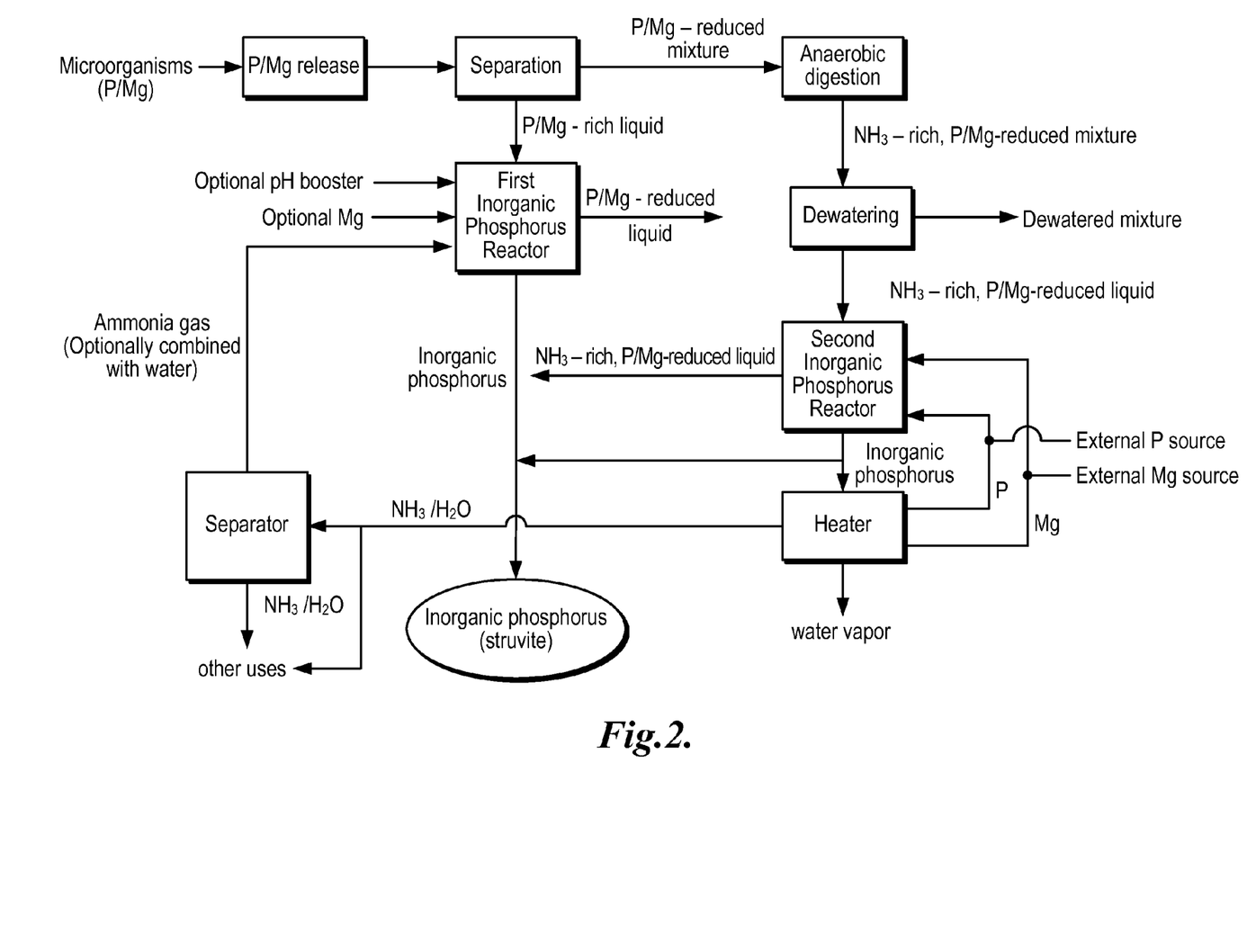
FIG. 2 is a schematic illustration of a representative method of the invention for treating wastewater and producing inorganic phosphorus.

A schematic illustration of a second embodiment of the method of the invention for treating wastewater and producing inorganic phosphorus is shown in FIG. 2. Referring to FIG. 2, a mixture of microorganisms containing phosphorus and magnesium are induced to release phosphorus and magnesium into liquid to provide a treated mixture that includes phosphorus and magnesium. The treated mixture is then thickened (dewatered) to provide a phosphorus- and magnesium-rich liquid and a phosphorus- and magnesium-reduced mixture. The phosphorus- and magnesium-rich liquid is conducted to a first inorganic phosphorus reactor. The phosphorus- and magnesium-reduced mixture is subjected to anaerobic digestion, where ammonia is released, to provide an ammonia-rich, phosphorus- and magnesium-reduced mixture containing suspended solids in liquid. Substantially no combination of phosphorus and magnesium occurs at this point because of the relatively low concentration of each and because the pH is low. A first ammonia-rich, phosphorus- and magnesium-reduced liquid is separated from the ammonia-rich, phosphorus- and magnesium-reduced mixture leaving behind a high biosolids portion. As noted above, separation of the liquid from the biosolids can be achieved by a variety of conventional means. The biosolids are removed from the system and the first ammonia-rich, phosphorus- and magnesium-reduced liquid is conducted to a second inorganic phosphorus reactor for inorganic phosphorus formation. There, phosphorus and/or magnesium is added, if needed (the sources for the phosphorus and magnesium are either external or from the inorganic phosphorus heater described below), and pH is adjusted (e.g., addition of sodium hydroxide or other suitable pH booster), if necessary, to provide inorganic phosphorus (e.g., struvite) and a second ammonia-rich, phosphorus- and magnesium-reduced liquid, which is removed from the system. The inorganic phosphorus is collected from the reactor and optionally directed to an inorganic phosphorus heater that provides ammonia and water, and magnesium, phosphorus, and water vapor. The water vapor is exhausted from the system and the magnesium and the phosphorus are conducted to the first inorganic phosphorus reactor to serve as inputs, as necessary. The ammonia and water are either converted for other uses (e.g., combined with sulfuric acid to provide ammonium sulfate, which can be added to inorganic phosphorus to provide a nitrogen boost) or directed to a separator to provide ammonia gas. The ammonia is then introduced into the first inorganic phosphorus reactor where it is combined with the phosphorus- and magnesium-rich liquid produced from the thickening of the treated mixture containing phosphorus and magnesium from the microorganism release step. Inorganic phosphorus (e.g., struvite) is formed in and ultimately collected from the first reactor. As an alternative to introducing ammonia gas to the first inorganic phosphorus reactor, ammonia gas from the stripper can be combined with water and the resulting water containing ammonia can be added to the first reactor. Alternatively, the water and ammonia from the heater can be used in a combined form (i.e., concentrated ammonia/water liquid mixture) thereby obviating the need for the separator. Additional ammonia (e.g., gas from external source) or other suitable pH boosters can be added to the first reactor, as necessary. Inorganic phosphorus formed in the first reactor can be optionally directed to the inorganic phosphorous heater to provide magnesium and phosphorus conducted to the first inorganic phosphorus reactor. In one embodiment, a phosphorus- and magnesium-reduced liquid produced by the first reactor is conducted from the reactor.

Thus, in one embodiment, the method includes the following steps:

(a) inducing a mixture of microorganisms containing phosphorus and magnesium to release phosphorus and magnesium to provide a treated mixture that includes phosphorus and magnesium;

(b) thickening the treated mixture to provide a phosphorus- and magnesium-rich liquid and a phosphorus- and magnesium-reduced mixture;

(c) conducting the phosphorus- and magnesium-rich liquid to a first inorganic phosphorus reactor;

(d) anaerobically treating the phosphorus- and magnesium-reduced mixture to provide an ammonia-rich, phosphorus- and magnesium-reduced mixture;

(e) separating a first ammonia-rich, phosphorus- and magnesium-reduced liquid from the ammonia-rich, phosphorus- and magnesium-reduced mixture;

(f) conducting the first ammonia-rich, phosphorus- and magnesium-reduced liquid to a second inorganic phosphorus reactor and optionally adjusting the pH (and optionally adding magnesium and/or phosphorus) to provide inorganic phosphorus (e.g., struvite);

(g) conducting a portion of the inorganic phosphorus from the second inorganic phosphorus reactor to a heater to provide magnesium, phosphorus, and ammonia and water, wherein the magnesium and phosphorus are optionally conducted to the second inorganic phosphorus reactor, and wherein the ammonia and water are added to the phosphorus- and magnesium-rich liquid in the first inorganic phosphorus reactor (optionally adjusting pH) to provide inorganic phosphorus (e.g., struvite); and (h) optionally conducting a portion of the inorganic phosphorus from the second inorganic phosphorus reactor to the heater in step (g).

In one embodiment, the ammonia and water are conducted to a separator to provide gaseous ammonia, which is optionally combined with water, that is added to the phosphorus- and magnesium-rich liquid in the first inorganic reactor.

Advantages of the process of the second embodiment include those noted above with regard to process of the first embodiment relating to the advantage associated with ammonia use. A further advantage of the process of the second embodiment is the additional recovery and re-use of magnesium, which can be used in the formation of inorganic phosphorus.

Figure 3:
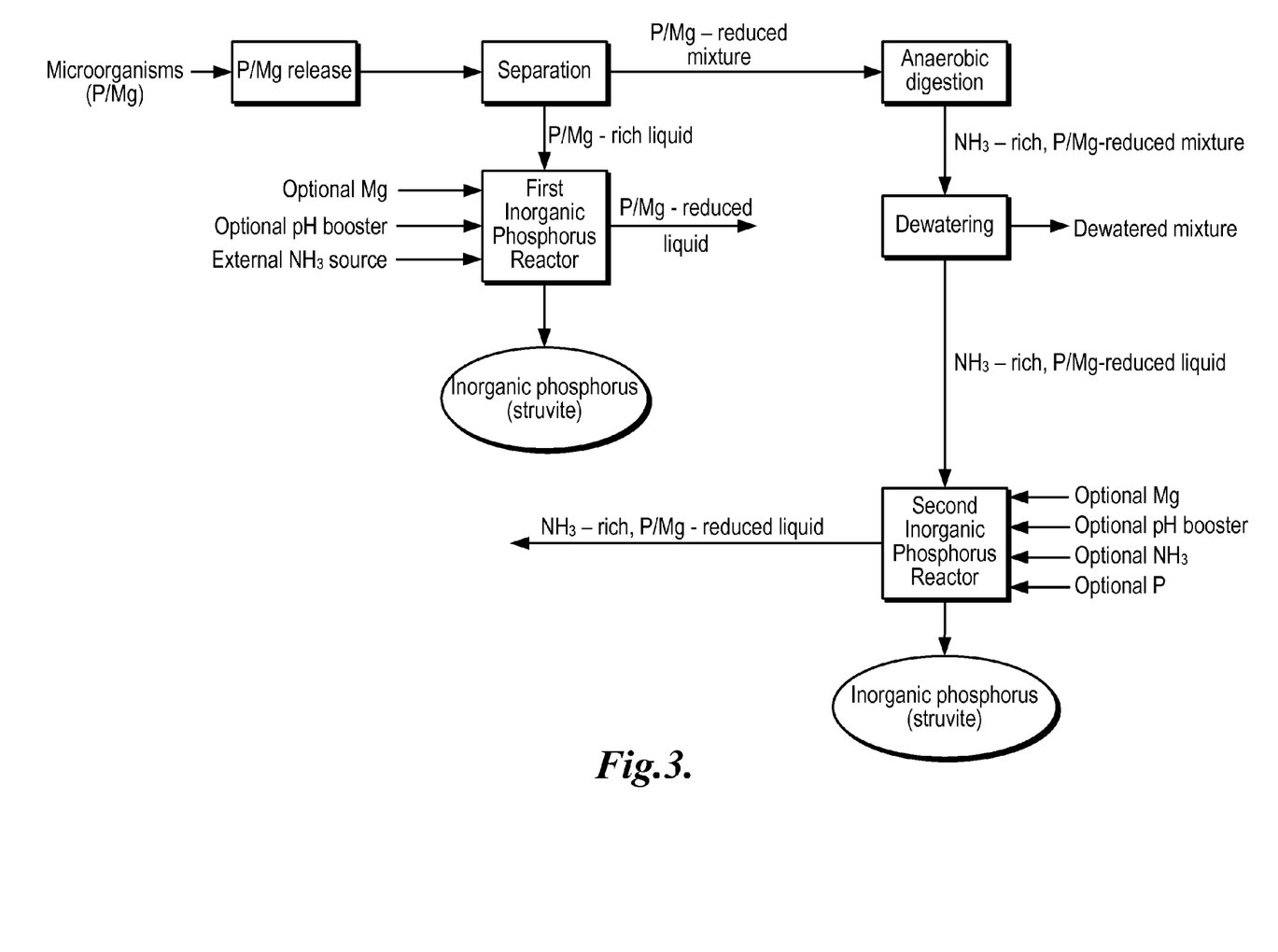
FIG. 3 is a schematic illustration of a representative method of the invention for treating wastewater and producing inorganic phosphorus.

A schematic illustration of a third embodiment of the method of the invention for treating wastewater and producing inorganic phosphorus is shown in FIG. 3. Referring to FIG. 3, a mixture of microorganisms containing phosphorus and magnesium are induced to release phosphorus and magnesium into liquid to provide a treated mixture that includes phosphorus and magnesium. The treated mixture is then thickened (dewatered) to provide a phosphorus- and magnesium-rich liquid and a phosphorus- and magnesium-reduced mixture. The phosphorus- and magnesium-rich liquid is conducted to a first inorganic phosphorus reactor. The phosphorus- and magnesium-reduced mixture is subjected to anaerobic digestion, where ammonia is released, to provide an ammonia-rich, phosphorus- and magnesium-reduced mixture. Substantially no combination of phosphorus and magnesium occurs because of the relatively low concentration of each and because the pH is low. A first ammonia-rich, phosphorus- and magnesium-reduced liquid is separated from the ammonia-rich, phosphorus- and magnesium-reduced mixture leaving behind a high biosolids portion. As noted above, separation of the liquid from the biosolids can be achieved by a variety of conventional means. The biosolids are removed from the system and the first ammonia-rich, phosphorus- and magnesium-reduced liquid is conducted to a second inorganic phosphorus reactor, where magnesium is added, if needed, and pH is adjusted (e.g., addition of sodium hydroxide or other suitable pH booster), if necessary, to provide inorganic phosphorus (e.g., struvite). The inorganic phosphorus is collected from the reactor and the high pH, second ammonia-rich, phosphorus- and magnesium-reduced liquid is removed from the system. Ammonia (e.g., gas) is introduced into a first inorganic phosphorus reactor where it is combined with the phosphorus- and magnesium-rich liquid produced from the thickening of the treated mixture containing phosphorus and magnesium from the microorganism release step. Inorganic phosphorus (e.g., struvite) is formed in and ultimately collected from the first reactor. Other suitable pH boosters can be added to the first reactor, as necessary. In one embodiment, a phosphorus- and magnesium-reduced liquid produced by the first reactor is conducted from the reactor.

Thus, in one embodiment, the method includes the following steps:

(a) inducing a mixture of microorganisms containing phosphorus and magnesium to release phosphorus and magnesium to provide a treated mixture that includes phosphorus and magnesium;

(b) thickening the treated mixture to provide a phosphorus- and magnesium-rich liquid and a phosphorus- and magnesium-reduced mixture;

(c) conducting the phosphorus- and magnesium-rich liquid to a first inorganic phosphorus reactor;

(d) adding ammonia to the phosphorus- and magnesium-rich liquid in the first inorganic phosphorus reactor (optionally adjusting pH) to provide inorganic phosphorus (e.g., struvite);

(e) anaerobically treating the phosphorus- and magnesium-reduced mixture from step (b) to provide an ammonia-rich, phosphorus- and magnesium-reduced mixture;

(f) separating a first ammonia-rich, phosphorus- and magnesium-reduced liquid from the ammonia-rich, phosphorus- and magnesium-reduced mixture; and (g) conducting the ammonia-rich, phosphorus- and magnesium-reduced liquid to a second inorganic phosphorus reactor and optionally adjusting the pH (and optionally adding magnesium, phosphorus, and/or ammonia, each from an external source) to provide inorganic phosphorus (e.g., struvite).

Advantages of the process of the third embodiment include those noted above with regard to process of the first and second embodiments relating to the advantage associated with ammonia use. A further advantage of the process of the third embodiment is the further decoupling of the two crystallizers and the greater production of useful struvite.

Figure 4:
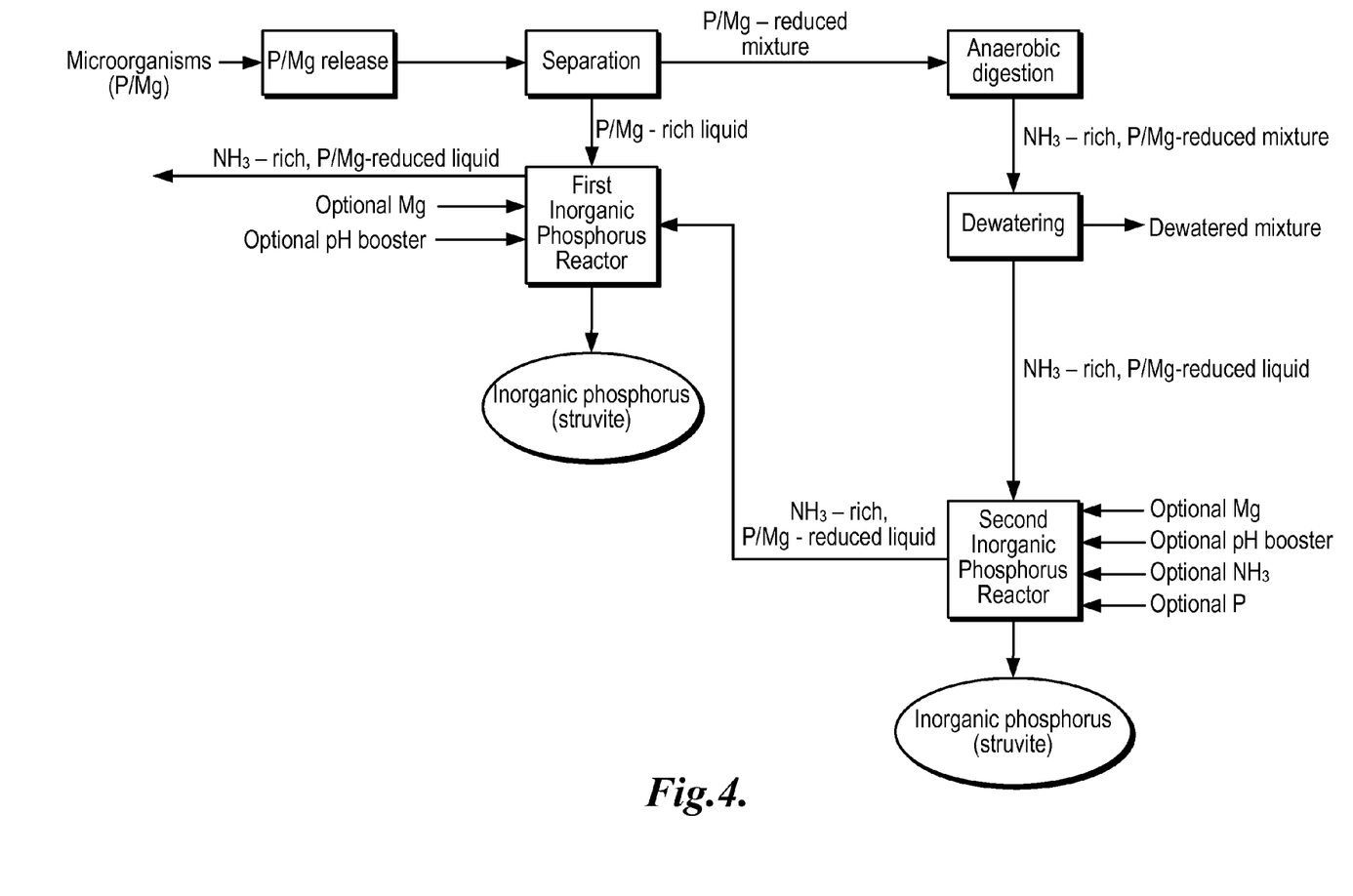
FIG. 4 is a schematic illustration of a representative method of the invention for treating wastewater and producing inorganic phosphorus.

A schematic illustration of a fourth embodiment of the method of the invention for treating wastewater and producing inorganic phosphorus is shown in FIG. 4. Referring to FIG. 4, a mixture of microorganisms containing phosphorus and magnesium are induced to release phosphorus and magnesium into liquid to provide a treated mixture that includes phosphorus and magnesium. The treated mixture is then thickened (dewatered) to provide a phosphorus- and magnesium-rich liquid and a phosphorus- and magnesium-reduced mixture. The phosphorus- and magnesium-rich liquid is conducted to a first inorganic phosphorus reactor. The phosphorus- and magnesium-reduced mixture is subjected to anaerobic digestion, where ammonia is released, to provide an ammonia-rich, phosphorus- and magnesium-reduced mixture. Substantially no combination of phosphorus and magnesium occurs because of the relatively low concentration of each and because the pH is low. A first ammonia-rich, phosphorus- and magnesium-reduced liquid is separated from the ammonia-rich, phosphorus- and magnesium-reduced mixture leaving behind a high biosolids portion. As noted above, separation of the liquid from the biosolids can be achieved by a variety of conventional means. The biosolids are removed from the system and the first ammonia-rich, phosphorus- and magnesium-reduced liquid is conducted to a second inorganic phosphorus reactor, where magnesium is added, if needed, and pH is adjusted (e.g., addition of sodium hydroxide or other suitable pH booster), if necessary, to provide inorganic phosphorus (e.g., struvite). The inorganic phosphorus is collected from the reactor and the high pH, second ammonia-rich, phosphorus- and magnesium-reduced liquid is conducted to the first inorganic phosphorus reactor where it is combined with the phosphorus- and magnesium-rich liquid produced from the thickening of the treated mixture containing phosphorus and magnesium from the microorganism release step. Inorganic phosphorus (e.g., struvite) is formed in and ultimately collected from the first reactor. Other suitable pH boosters and magnesium can be added to the first reactor, as necessary. In one embodiment, a phosphorus- and magnesium-reduced liquid produced by the first reactor is conducted from the reactor.

Thus, in one embodiment, the method includes the following steps:

(a) inducing a mixture of microorganisms containing phosphorus and magnesium to release phosphorus and magnesium to provide a treated mixture that includes phosphorus and magnesium;

(b) thickening the treated mixture to provide a phosphorus- and magnesium-rich liquid and a phosphorus- and magnesium-reduced mixture;

(c) conducting the phosphorus- and magnesium-rich liquid to a first inorganic phosphorus reactor;

(d) anaerobically treating the phosphorus- and magnesium-reduced mixture from step (b) to provide an ammonia-rich, phosphorus- and magnesium-reduced mixture;

(e) separating a first ammonia-rich, phosphorus- and magnesium-reduced liquid from the ammonia-rich, phosphorus- and magnesium-reduced mixture;

(f) conducting the first ammonia-rich, phosphorus- and magnesium-reduced liquid to a second inorganic phosphorus reactor and optionally adjusting the pH (and optionally adding magnesium, phosphorus, and/or ammonia, each from an external source) to provide inorganic phosphorus (e.g., struvite) and a second ammonia-rich, phosphorus- and magnesium-reduced liquid; and (g) conducting the second ammonia-rich, phosphorus- and magnesium-reduced liquid to the first inorganic phosphorus reactor (optionally adjusting pH) to provide inorganic phosphorus (e.g., struvite).

For the methods described herein in which an ammonia-rich, phosphorus- and magnesium-reduced liquid produced from the second inorganic phosphorus reactor is conducted to the first reactor, it will be appreciated that the amount of ammonia required for inorganic phosphorus production in the first inorganic reactor may be less than the amount of ammonia present in the ammonia-rich, phosphorus- and magnesium-reduced liquid produced from the second inorganic phosphorus reactor. Accordingly, in some embodiments, only a portion of the ammonia-rich, phosphorus- and magnesium-reduced liquid produced from the second inorganic phosphorus reactor is conducted to the first reactor.

In another aspect, the invention provides systems for treating wastewater and producing inorganic phosphorus.

Figure 5:
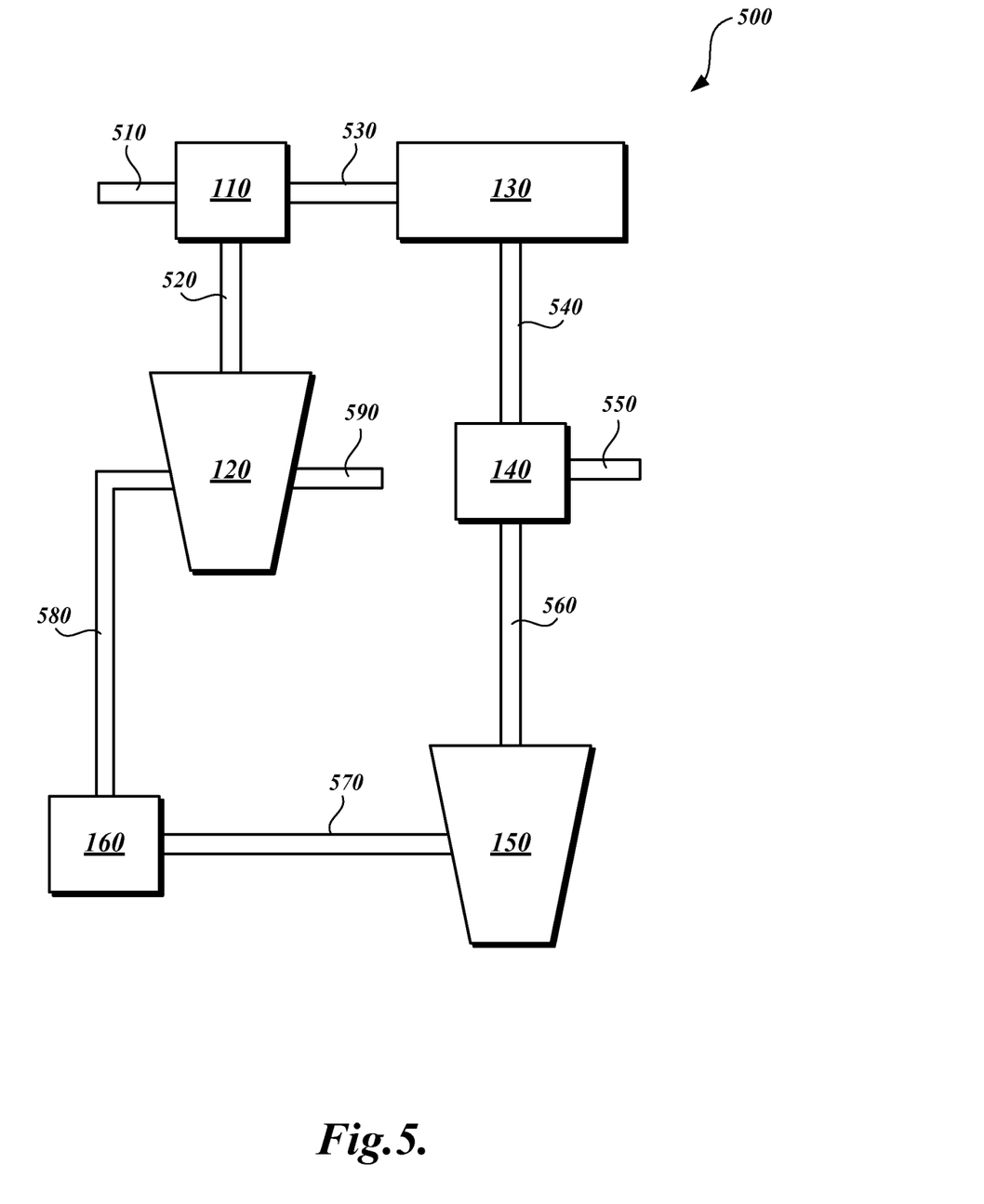
FIG. 5 is a schematic illustration of a representative system of the invention for treating wastewater and producing inorganic phosphorus.

Referring to FIG. 5, in one embodiment, the system (500) for producing inorganic phosphorus from wastewater, comprises:

(a) a first solids separator (110) for thickening a phosphorus- and magnesium-containing mixture derived from microorganisms induced to release phosphorus and magnesium to provide a phosphorus- and magnesium-rich liquid and a phosphorus- and magnesium-reduced mixture;

(b) a first inorganic reactor (120) for producing inorganic phosphorus;

(c) a first conduit (520) intermediate the first solids separator and the first inorganic phosphorus reactor for conducting the phosphorus- and magnesium-rich liquid to the first inorganic phosphorus reactor;

(d) a digester (130) for anaerobically treating the phosphorus- and magnesium-reduced mixture to provide an ammonia-rich, phosphorus- and magnesium-reduced mixture;

(e) a second conduit (530) intermediate the first solids separator and the digester for conducting the phosphorus- and magnesium-reduced mixture to the digester;

(f) a second solids separator (140) for separating a first ammonia-rich, phosphorus- and magnesium-reduced liquid from the ammonia-rich, phosphorus- and magnesium-reduced mixture;

(g) a second inorganic reactor (150) for producing inorganic phosphorus; and (h) a third conduit (540) intermediate the second solids separator and the second inorganic phosphorus reactor for conducting the first ammonia-rich, phosphorus- and magnesium-reduced liquid to the second inorganic phosphorus reactor.

In one embodiment, the first solids separator further comprises a conduit (510) for receiving a phosphorus- and magnesium-containing mixture.

In one embodiment, the second solids separator further comprises a conduit (550) for conducting biosolids from the solids separator.

In one embodiment, the first reactor further comprises a conduit (590) for conducting a phosphorus- and magnesium-reduced liquid from the reactor In one embodiment, the system (500) further comprises:

(a) an ammonia stripper (160) intermediate the first and second inorganic phosphorus reactors;

(b) a conduit (570) intermediate the second inorganic phosphorus reactor and the stripper for conducting a second ammonia-rich, phosphorus- and magnesium-reduced liquid from the second inorganic phosphorus reactor to the stripper; and (c) a conduit (580) intermediate the stripper and the first inorganic phosphorus reactor and the stripper for conducting ammonia from the stripper to the first inorganic phosphorus reactor. See FIGS. 1 and 5.

Figure 6:
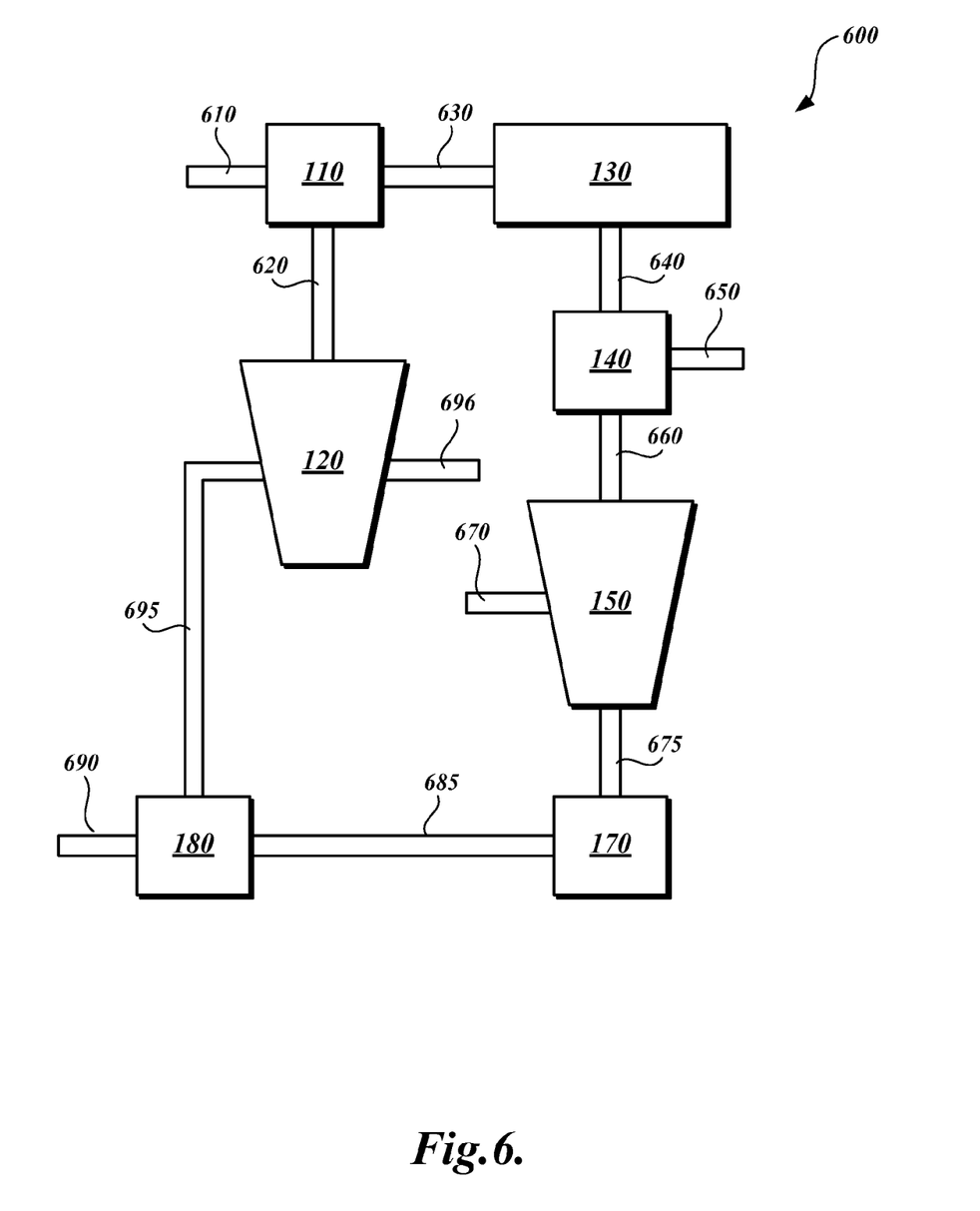
FIG. 6 is a schematic illustration of a representative system of the invention for treating wastewater and producing inorganic phosphorus.

In one embodiment, the system further comprises:

(a) a heater intermediate the first and second inorganic reactors for producing ammonia and water from inorganic phosphorus from the second inorganic phosphorus reactor;

(b) a conduit intermediate the second inorganic phosphorus reactor and the heater for conducting inorganic phosphorus from the second inorganic phosphorus reactor to the heater;

(c) a separator intermediate the heater and the first inorganic reactor for producing ammonia from the ammonia and water produced by the heater;

(d) a conduit intermediate the heater and the separator for conducting ammonia and water from the heater to the separator; and (e) a conduit intermediate the separator and first inorganic phosphorus reactor for conducting ammonia from the separator to the first inorganic phosphorus reactor. See FIGS. 2 and 6.

Referring to FIG. 6, system 600 includes:

(a) a first solids separator (110);

(b) a first inorganic reactor (120);

(c) a first conduit (620) intermediate the first solids separator and the first inorganic phosphorus reactor;

(d) a digester (130);

(e) a second conduit (630) intermediate the first solids separator and the digester;

(f) a second solids separator (140);

(g) a third conduit (640) intermediate the digester and the second solids separator;

(h) a second inorganic reactor (150);

(i) a third conduit (660) intermediate the second solids separator and the second inorganic phosphorus reactor;

(j) a heater (170) for producing ammonia and water from inorganic phosphorus from the second inorganic phosphorus reactor;

(k) a conduit (675) intermediate the second inorganic phosphorus reactor and the heater for conducting inorganic phosphorus from the second inorganic phosphorus reactor to the heater;

(l) a separator (180) for producing ammonia from the ammonia and water produced by the heater;

(m) a conduit (685) intermediate the heater and the separator for conducting ammonia and water from the heater to the separator; and (n) a conduit (695) intermediate the separator and first inorganic phosphorus reactor for conducting ammonia from the separator to the first inorganic phosphorus reactor.

In one embodiment, the first solids separator further comprises a conduit (610) for receiving a phosphorus- and magnesium-containing mixture.

In one embodiment, the second solids separator further comprises a conduit (650) for conducting biosolids from the solids separator.

In one embodiment, the first reactor further comprises a conduit (696) for conducting a phosphorus- and magnesium-reduced liquid from the reactor.

In another embodiment, the second inorganic phosphorus reactor further comprises a conduit for conducting a second ammonia-rich, phosphorus- and magnesium-reduced liquid from the second inorganic phosphorus reactor, and the first inorganic phosphorus reactor further comprises a conduit for receiving ammonia and a conduit for conducting a phosphorus- and magnesium-reduced liquid from the reactor. See FIGS. 3 and 7.

Figure 7:
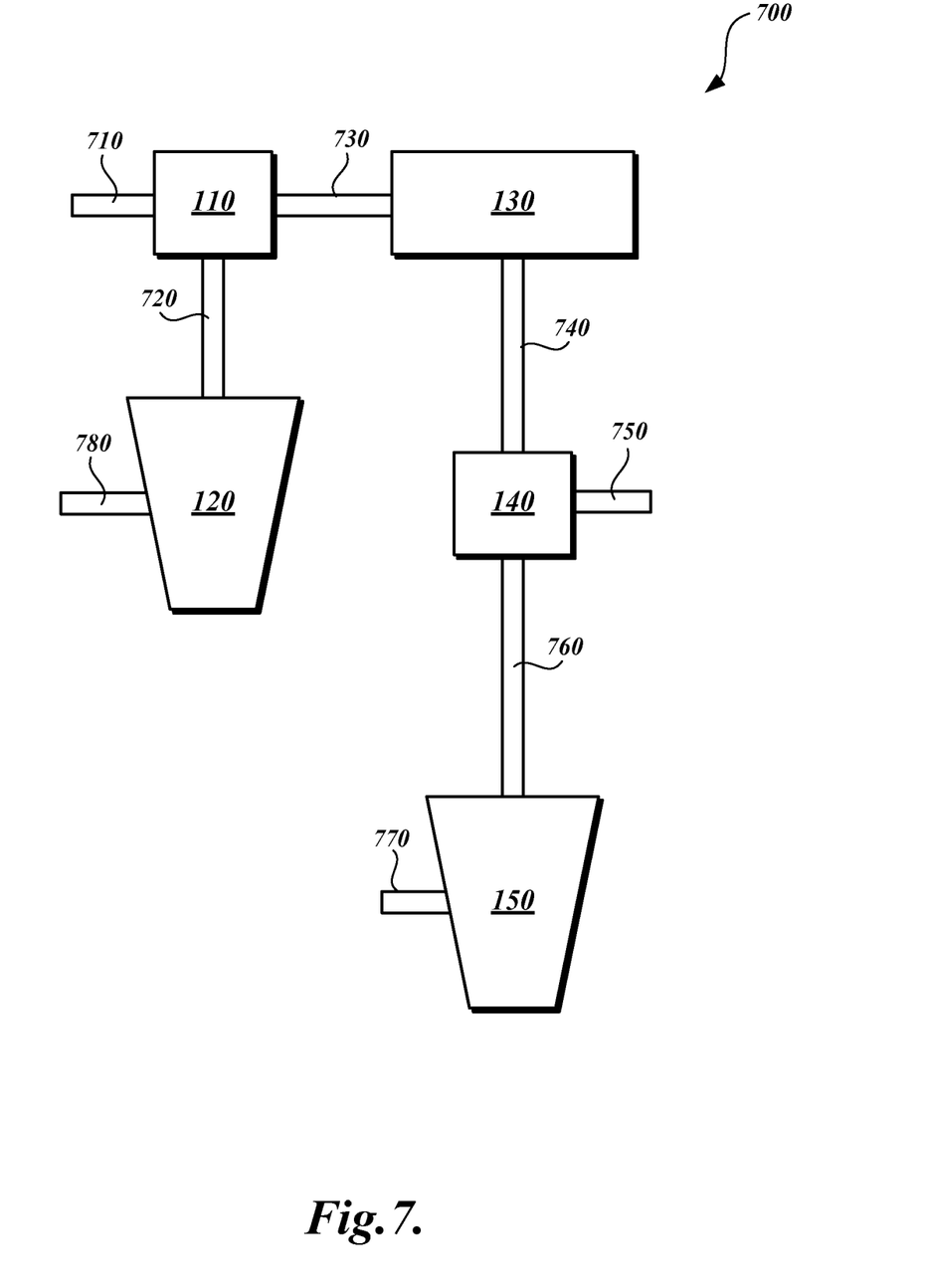
FIG. 7 is a schematic illustration of a representative system of the invention for treating wastewater and producing inorganic phosphorus.

Referring to FIG. 7, system 700 includes:

(a) a first solids separator (110);

(b) a first inorganic reactor (120);

(c) a first conduit (720) intermediate the first solids separator and the first inorganic phosphorus reactor;

(d) a digester (130);

(e) a second conduit (730) intermediate the first solids separator and the digester;

(f) a second solids separator (140);

(g) a third conduit (740) intermediate the digester and the second solids separator;

(h) a second inorganic reactor (150); and
(i) a third conduit (760) intermediate the second solids separator and the second inorganic phosphorus reactor.

In one embodiment, the first solids separator further comprises a conduit (710) for receiving a phosphorus- and magnesium-containing mixture.

In one embodiment, the second solids separator further comprises a conduit (750) for conducting biosolids from the solids separator.

In one embodiment, the first reactor further comprises a conduit (780) for conducting a phosphorus- and magnesium-reduced liquid from the reactor.

In a further embodiment, the system further comprises a conduit intermediate the second inorganic phosphorus reactor and the first inorganic phosphorus reactor for conducting a second ammonia-rich, phosphorus- and magnesium-reduced liquid from the second inorganic phosphorus reactor to the first inorganic phosphorus reactor; and the first inorganic phosphorus reactor further comprises a conduit for conducting a phosphorus- and magnesium-reduced liquid from the first inorganic phosphorus reactor. See FIGS. 4 and 8.

Figure 8:
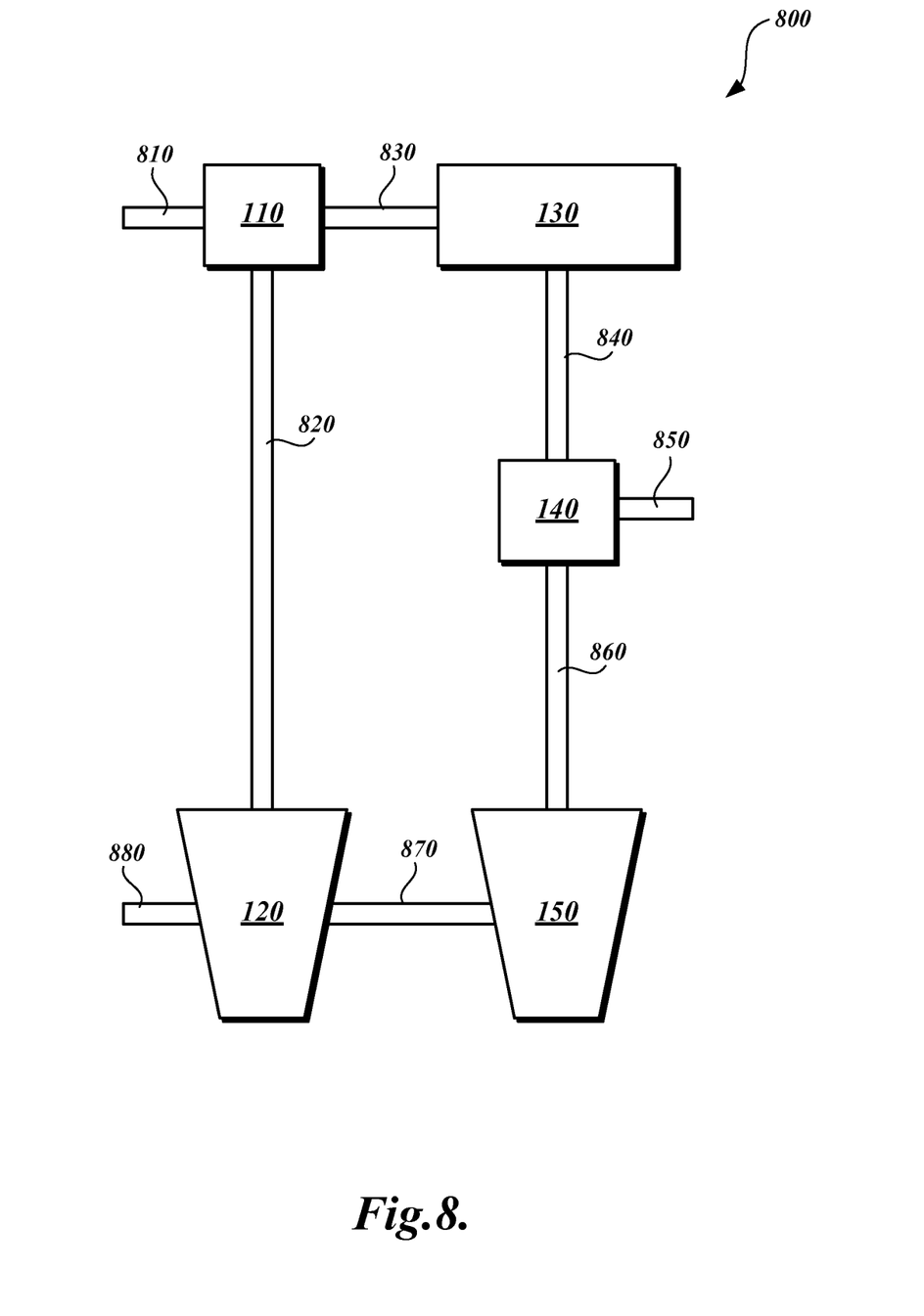
FIG. 8 is a schematic illustration of a representative system of the invention for treating wastewater and producing inorganic phosphorus.

Referring to FIG. 8, system 800 includes:
(a) a first solids separator (110);
(b) a first inorganic reactor (120);
(c) a first conduit (820) intermediate the first solids separator and the first inorganic phosphorus reactor;
(d) a digester (130);
(e) a second conduit (830) intermediate the first solids separator and the digester;
(f) a second solids separator (140);
(g) a third conduit (840) intermediate the second solids separator and the second inorganic phosphorus reactor;
(h) a second inorganic reactor (150);
(i) a third conduit (860) intermediate the second solids separator and the second inorganic phosphorus reactor; and
(j) a conduit (870) intermediate the second inorganic phosphorus reactor and the first inorganic phosphorus reactor for conducting a second ammonia-rich, phosphorus- and magnesium-reduced liquid from the second inorganic phosphorus reactor to the first inorganic phosphorus reactor.

In one embodiment, the first solids separator further comprises a conduit (810) for receiving a phosphorus- and magnesium-containing mixture.

In one embodiment, the second solids separator further comprises a conduit (850) for conducting biosolids from the solids separator.

In one embodiment, the first reactor further comprises a conduit (880) for conducting a phosphorus- and magnesium-reduced liquid from the reactor.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for producing inorganic phosphorus from wastewater, comprising:
   (a) thickening a phosphorus- and magnesium-containing mixture derived from microorganisms induced to release phosphorus and magnesium to provide a phosphorus- and magnesium-rich liquid and a phosphorus- and magnesium-reduced mixture;
   (b) conducting the phosphorus- and magnesium-rich liquid to a first inorganic phosphorus reactor;
   (c) anaerobically treating the phosphorus- and magnesium-reduced mixture to provide an ammonia-rich, phosphorus- and magnesium-reduced mixture;
   (d) separating a first ammonia-rich, phosphorus- and magnesium-reduced liquid from the ammonia-rich, phosphorus- and magnesium-reduced mixture;
   (e) conducting the first ammonia-rich, phosphorus- and magnesium-reduced liquid to a second inorganic phosphorus reactor to provide inorganic phosphorus and a second ammonia-rich, phosphorus- and magnesium-reduced liquid; and
   (f) adding ammonia to the phosphorus- and magnesium-rich liquid in the first inorganic phosphorus reactor to provide inorganic phosphorus.

2. The method of claim 1, wherein the ammonia added to the phosphorus- and magnesium-rich liquid in the first inorganic phosphorus reactor is derived from the second ammonia-rich, phosphorus- and magnesium-reduced liquid.

3. The method of claim 1, wherein the ammonia added to the phosphorus- and magnesium-rich liquid in the first inorganic phosphorus reactor is derived from the inorganic phosphorus provided in the second inorganic phosphorus reactor.

4. The method of claim 1, wherein the ammonia added to the phosphorus- and magnesium-rich liquid in the first inorganic phosphorus reactor is from an external source.

5. The method of claim 1, wherein the ammonia added to the phosphorus- and magnesium-rich liquid in the first inorganic phosphorus reactor is an ammonia-rich, phosphorus- and magnesium-reduced liquid from the second inorganic phosphorus reactor.

6. A method for treating wastewater and producing inorganic phosphorus, comprising:
   (a) inducing a mixture of microorganisms containing phosphorus and magnesium to release phosphorus and magnesium to provide a treated mixture that includes phosphorus and magnesium;
   (b) thickening the treated mixture to provide a phosphorus- and magnesium-rich liquid and a phosphorus- and magnesium-reduced mixture;
   (c) conducting the phosphorus- and magnesium-rich liquid to a first inorganic phosphorus reactor;
   (d) anaerobically treating the phosphorus- and magnesium-reduced mixture to provide an ammonia-rich, phosphorus- and magnesium-reduced mixture;
   (e) separating a first ammonia-rich, phosphorus- and magnesium-reduced liquid from the ammonia-rich, phosphorus- and magnesium-reduced mixture;
   (f) conducting the first ammonia-rich, phosphorus- and magnesium-reduced liquid to a second inorganic phosphorus reactor to provide inorganic phosphorus and a second ammonia-rich, phosphorus- and magnesium-reduced liquid;
   (g) conducting the second ammonia-rich, phosphorus- and magnesium-reduced liquid to an ammonia stripper to provide ammonia and an ammonia-reduced, phosphorus-, and magnesium-reduced liquid; and
   (h) adding the ammonia to the phosphorus- and magnesium-rich liquid in the first inorganic phosphorus reactor to provide inorganic phosphorus.

7. The method of claim 6 further comprising adjusting the pH of the ammonia-rich, phosphorus- and magnesium-reduced liquid in the second inorganic phosphorus reactor.

8. The method of claim 6 further comprising adding magnesium to the ammonia-rich, phosphorus- and magnesium-reduced liquid in the second inorganic phosphorus reactor.

9. The method of claim 6, wherein the inorganic phosphorus is a magnesium/phosphate complex.

10. The method of claim 6, wherein the inorganic phosphorus is a magnesium ammonium phosphate hexahydrate.

11. The method of claim 6, wherein the inorganic phosphorus is struvite.

12. A method for treating wastewater and producing inorganic phosphorus, comprising:
(a) inducing a mixture of microorganisms containing phosphorus and magnesium to release phosphorus and magnesium to provide a treated mixture that includes phosphorus and magnesium;
(b) thickening the treated mixture to provide a phosphorus- and magnesium-rich liquid and a phosphorus- and magnesium-reduced mixture;
(c) conducting the phosphorus- and magnesium-rich liquid to a first inorganic phosphorus reactor;
(d) anaerobically treating the phosphorus- and magnesium-reduced mixture to provide an ammonia-rich, phosphorus- and magnesium-reduced mixture;
(e) separating a first ammonia-rich, phosphorus- and magnesium-reduced liquid from the ammonia-rich, phosphorus- and magnesium-reduced mixture;
(f) conducting the first ammonia-rich, phosphorus- and magnesium-reduced liquid to a second inorganic phosphorus reactor to provide inorganic phosphorus; and
(g) conducting a portion of the inorganic phosphorus from the second inorganic phosphorus reactor to a heater to provide magnesium, phosphorus, and ammonia and water, wherein the ammonia is added to the phosphorus- and magnesium-rich liquid in the first inorganic phosphorus reactor to provide inorganic phosphorus.

13. The method of claim 12, wherein the ammonia and optionally water from the heater are conducted to a separator to provide gaseous ammonia, which is then optionally combined with water, and added to the phosphorus- and magnesium-rich liquid in the first inorganic phosphorus reactor.

14. The method of claim 12 further comprising adding magnesium to the ammonia-rich, phosphorus- and magnesium-reduced liquid in the second inorganic phosphorus reactor.

15. The method of claim 14, wherein the magnesium is provided from the inorganic phosphorus in the heater to the second inorganic phosphorus reactor.

16. The method of claim 12 further comprising adding phosphorus to the ammonia-rich, phosphorus- and magnesium-reduced liquid in the second inorganic phosphorus reactor.

17. The method of claim 16, wherein the phosphorus is provided from the inorganic phosphorus in the heater to the second inorganic phosphorus reactor.

18. The method of claim 12 further comprising conducting a portion of the inorganic phosphorus from the first inorganic phosphorus reactor to the heater.

19. A method for treating wastewater and producing inorganic phosphorus, comprising:
(a) inducing a mixture of microorganisms containing phosphorus and magnesium to release phosphorus and magnesium to provide a treated mixture that includes phosphorus and magnesium;
(b) thickening the treated mixture to provide a phosphorus- and magnesium-rich liquid and a phosphorus- and magnesium-reduced mixture;
(c) conducting the phosphorus- and magnesium-rich liquid to a first inorganic phosphorus reactor;
(d) adding ammonia to the phosphorus- and magnesium-rich liquid in the first inorganic phosphorus reactor to provide inorganic phosphorus;
(e) anaerobically treating the phosphorus- and magnesium-reduced mixture from step (b) to provide an ammonia-rich, phosphorus- and magnesium-reduced mixture;
(f) separating a first ammonia-rich, phosphorus- and magnesium-reduced liquid from the ammonia-rich, phosphorus- and magnesium-reduced mixture; and
(g) conducting the first ammonia-rich, phosphorus- and magnesium-reduced liquid to a second inorganic phosphorus reactor to provide inorganic phosphorus.

20. A method for treating wastewater and producing inorganic phosphorus, comprising:
(a) inducing a mixture of microorganisms containing phosphorus and magnesium to release phosphorus and magnesium to provide a treated mixture that includes phosphorus and magnesium;
(b) separating the treated mixture into a phosphorus- and magnesium-rich liquid and a phosphorus- and magnesium-reduced mixture;
(c) conducting the phosphorus- and magnesium-rich liquid to a first inorganic phosphorus reactor;
(d) anaerobically treating the phosphorus- and magnesium-reduced mixture to provide an ammonia-rich, phosphorus- and magnesium-reduced mixture;
(e) separating the ammonia-rich, phosphorus- and magnesium-reduced mixture to provide biosolids and a first ammonia-rich, phosphorus- and magnesium-reduced liquid;
(f) conducting the first ammonia-rich, phosphorus- and magnesium-reduced liquid to a second inorganic phosphorus reactor to provide inorganic phosphorus and a second ammonia-rich, phosphorus- and magnesium-reduced liquid; and
(g) conducting the second ammonia-rich, phosphorus- and magnesium-reduced liquid to the first inorganic phosphorus reactor to provide inorganic phosphorus and a third ammonia-rich, phosphorus- and magnesium-reduced liquid.

21. A system for producing inorganic phosphorus from wastewater, comprising:
(a) a first solids separator for thickening a phosphorus- and magnesium-containing mixture;
(b) a first inorganic reactor, the reactor having a conduit for receiving ammonia;
(c) a first conduit intermediate the first solids separator and the first inorganic phosphorus reactor;
(d) a digester;
(e) a second conduit intermediate the first solids separator and the digester;
(f) a second solids separator;
(g) a third conduit intermediate the digester and the second solids separator;
(h) a second inorganic reactor; and
(i) a fourth conduit intermediate the second solids separator and the second inorganic phosphorus reactor.

22. The method of claim 20, wherein a portion of the ammonia-rich, phosphorus- and magnesium-reduced liquid produced from the second inorganic phosphorus reactor is conducted to the first reactor.

23. The method of claim 20 further comprising adjusting the pH of the first ammonia-rich, phosphorus- and magnesium-reduced liquid in the second inorganic phosphorus reactor.

24. The method of claim 20 further comprising adding magnesium to the first ammonia-rich, phosphorus- and magnesium-reduced liquid in the second inorganic phosphorus reactor.

25. The method of claim 20 further comprising adding phosphorus to the first ammonia-rich, phosphorus- and magnesium-reduced liquid in the second inorganic phosphorus reactor.

26. The method of claim 20 further comprising adding ammonia to the first ammonia-rich, phosphorus- and magnesium-reduced liquid in the second inorganic phosphorus reactor.

27. The method of claim 20 further comprising adjusting the pH of the second ammonia-rich, phosphorus- and magnesium-reduced liquid in the first inorganic phosphorus reactor.

28. The method of claim 20 further comprising adding magnesium to the second ammonia-rich, phosphorus- and magnesium-reduced liquid in the first inorganic phosphorus reactor.

29. The method of claim 1, wherein the inorganic phosphorus is struvite.

30. The method of claim 12, wherein the inorganic phosphorus is struvite.

31. The method of claim 19, wherein the inorganic phosphorus is struvite.

32. The method of claim 20, wherein the inorganic phosphorus is struvite.

33. The system of claim 21, wherein the first solids separator further comprises a conduit for receiving a phosphorus- and magnesium-containing mixture.

34. The system of claim 21, wherein the second solids separator further comprises a conduit for conducting biosolids from the solids separator.

35. The system of claim 21 further comprising:
(a) an ammonia stripper intermediate the first and second inorganic phosphorus reactors;
(b) a conduit intermediate the second inorganic phosphorus reactor and the stripper; and
(c) a conduit intermediate the stripper and the first inorganic phosphorus reactor and the stripper.

36. The system of claim 21 further comprising:
(a) a heater intermediate the first and second inorganic phosphorus reactors;
(b) a conduit intermediate the second inorganic phosphorus reactor and the heater;
(c) an ammonia separator intermediate the first and second inorganic phosphorus reactors;
(d) a conduit intermediate the heater and the separator; and
(e) a conduit intermediate the separator and first inorganic phosphorus reactor.

37. The system of claim 21, wherein the second inorganic phosphorus reactor further comprises a conduit for conducting an ammonia-rich, phosphorus- and magnesium-reduced liquid from the second inorganic phosphorus reactor.

38. The system of claim 21, wherein the first inorganic phosphorus reactor further comprises a conduit for receiving ammonia.

39. The system of claim 21 further comprising a conduit intermediate the second inorganic phosphorus reactor and the first inorganic phosphorus reactor.

40. The system of claim 21 further comprising a conduit for conducting a phosphorus- and magnesium-reduced liquid from the first inorganic phosphorus reactor.

* * * * *